United States Patent
Hoke et al.

(10) Patent No.: US 10,273,451 B2
(45) Date of Patent: Apr. 30, 2019

(54) IMMORTALIZATION OF CELLS INCLUDING NEURONAL CELLS

(71) Applicant: The Johns Hopkins University, Baltimore, MD (US)

(72) Inventors: Ahmet Hoke, Towson, MD (US); Weiran Chen, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/598,955

(22) Filed: Jan. 16, 2015

(65) Prior Publication Data

US 2015/0175963 A1 Jun. 25, 2015

Related U.S. Application Data

(63) Continuation of application No. 11/918,622, filed as application No. PCT/US2006/014247 on Apr. 14, 2006, now abandoned.

(60) Provisional application No. 60/671,865, filed on Apr. 15, 2005.

(51) Int. Cl.
*C12N 5/0793* (2010.01)
*C12N 9/12* (2006.01)
*G01N 33/50* (2006.01)

(52) U.S. Cl.
CPC ......... *C12N 5/0619* (2013.01); *C12N 9/1276* (2013.01); *G01N 33/5058* (2013.01); *C12N 2510/04* (2013.01); *C12N 2799/027* (2013.01); *G01N 2500/10* (2013.01)

(58) Field of Classification Search
None
See application file for complete search history.

(56) References Cited

U.S. PATENT DOCUMENTS

| 5,571,791 A * | 11/1996 | Thompson | C07K 14/721 435/69.1 |
| 6,399,384 B1 | 6/2002 | Jat | |
| 2004/0259197 A1* | 12/2004 | Suppmann | C12N 9/22 435/69.1 |
| 2005/0032213 A1 | 2/2005 | Sinden et al. | |

OTHER PUBLICATIONS

Pilcher et al (Soc Neurosc Meeting abstract 27: pp. 1525, 2001 (abstract only).*
Haas et al Neuron, 29: 583-591, 2001.*
Karra et al. (J. Neurosc 30: 6171-6177, 2010).*
Teruel et al (J Neurosc Meth 93: 37-48, 1999).*
Mellon et al (Neuron 5:1-10, 1990).
White et al (J Neurosc 14: 6744-6753, 1994).
Weiner et al. Front Neuroendocrinol 13: 95-119, 1992; abstract.
Bar et al Neurosc Lett 361: 172-175, 2004.
Barad et al. PNAS 95: 15020-15025, 1998.
Whittemore et al (Glia 10:211-26, 1994—abstract only).
Raymon et al (The Jour Neurosc 19: 5420-5428, 1999).
Wilby et al (The Jour Neurosc 19:2301-2312, 1999).

* cited by examiner

*Primary Examiner* — Daniel E Kolker
*Assistant Examiner* — Aditi Dutt
(74) *Attorney, Agent, or Firm* — Mintz Levin Cohn Ferris Glovsky and Popeo, P.C.; Peter F. Corless

(57) ABSTRACT

The instant invention provides methods for immortalizing cells. The invention further provides immortalized cell lines, e.g., neuronal cell lines, and methods of using these cell lines in screening assays.

20 Claims, 5 Drawing Sheets

Specification includes a Sequence Listing.

IMMORTALIZATION OF CELLS INCLUDING NEURONAL CELLS

RELATED APPLICATIONS

This application is a continuation of U.S. Utility application Ser. No. 11/918,622, filed Jan. 27, 2009, now abandoned, which is the U.S. national stage application filed under 35 U.S.C. § 371, of International Application No. PCT/US2006/014247, filed Apr. 14, 2006, and published on Oct. 26, 2006 as Publication No. WO 2006/113534 which claims the benefit of U.S. Provisional Application No. 60/671,865, filed Apr. 15, 2005. The entire contents of the preceding applications are incorporated herein by reference.

GOVERNMENT SUPPORT

The following invention was supported at least in part by NIH Grants RO1 NS43991 and PO1 MH70056. Accordingly, the government may have certain rights in the invention.

BACKGROUND OF THE INVENTION

Neuropathic pain, also referred to as a chronic pain, is a complex disorder resulting from injury to the nerve, spinal cord or brain. There is evidence that nerve fibers in subjects with neuropathic pain develop abnormal excitability, particularly hyper-excitability, Zimmerman (2001) Eur J Pharmacol 429 (1-3):23-37. Although the American Pain Society estimates that nearly 50 million Americans are totally or partially disabled by pain, there are currently very few effective, well-tolerated treatments available (Wetzel et al. (1997) Ann Pharmacother 31 (9):1082-3). Indeed, existing therapeutics cause a range of undesirable side effects primarily due to the difficulty in developing small-molecule drugs capable of specifically targeting the receptor/channel of choice.

Many, relatively common clinical conditions are associated with neuropathic pain (Berger A, et al. (2004) J Pain 5:143-149). Traditionally, combinations of tricyclic antidepressants or anti-epileptics along with analgesics have been used to treat neuropathic pain (reviewed in (Mendell J et al. (2003) N Engl J Med 348:1243-1255). However, treatment of neuropathic pain is often unsatisfactory; persistent neuropathic pain affects quality of life and lead to significant morbidity. In recent years with the identification of the receptor for capsaicin (Caterina M J et al. (1997) Nature 389:816-824; Caterina, M J et al. (2000) Science 288:306-313), neuropathic pain research has directed its attention to identification of drugs that interfere with the transient receptor potential vanilloid receptor 1 (TRPV1) physiology. Primary effort has focused on antagonists that block nociceptive pain sensation at the receptor level but so far, no drug has reached clinical use (Caterina M J et al. (1997) Nature 389:816-824 and Caterina, M J et al. (2000) Science 288:306-313)

Previous attempts at identifying TRPV1 antagonists have used non-neuronal cell lines expressing recombinant TRPV1 and the calcium flux induced by capsaicin as an outcome measure for high throughput screening (HTS) (Caterina M J et al. (1997) Nature 389:816-824; Caterina, M J et al. (2000) Science 288:306-313). Although these cells expressing recombinant TRPV1 may be useful, a nociceptive sensory neuronal cell expressing TRPV1 might be more relevant because the non-neuronal cell lines may lack the appropriate intracellular signaling pathways associated with and downstream of TRPV1 in nociceptive sensory neurons. In order to generate tools for a more rational approach to drug screening for neuropathic pain, it would be useful to have an immortalized DRG sensory neuronal line with nociceptive properties. To date, attempts to immortalize neuronal cell lines have achieved little success.

Likewise, the ability to generate immortalized cell lines using cells that have been historically difficult to immortalize would be beneficial in the efforts to develop novel therapeutics for the treatment of disease and illness.

Although neuronal cell lines have been generated in the past these were mostly from embryonic tissues and were derived from progenitor or stem cells (see, e.g., Bernard J (1989) *Neurosci Res,* 24:9-20, Evrard (1990) *PNAS,* 87:3062-6, Redies J (1991) *Neurosci Res* 30:601-15). Also, a temperature sensitive mutant T antigen has been used to immortalize neuronal populations, but the efficiency of this technique has been very low (Eves (1994) *Brain Res* 656: 396-404).

Accordingly, the need exists for effective and reliable methods of immortalizing cells that scientists have not had success in immortalizing with currently available methods, e.g., neuronal cells.

SUMMARY OF THE INVENTION

The instant invention is directed to methods for making immortalized cell lines from cells that are historically difficult to immortalize, e.g., neuronal cells. The inventors of the instant application have discovered a novel method for making stable immortalized cells, e.g., neuronal cells.

Accordingly, in one aspect the instant invention provides, methods for generating an immortalized human cell comprising introducing into a cell a DNA segment encoding an oncogene, selecting for a cell containing the DNA segment, and introducing hTERT into the selected cell, thereby generating an immortalized cell.

In one embodiment, the DNA segment is contained in a plasmid. In another embodiment, hTERT is contained in a plasmid.

In another embodiment, the neuronal cells are selected from a group consisting of neuronal cells from the brain, neuronal cells from the spinal cord, dorsal root sensory ganglia, dorsal root ganglia neuron and autonomic ganglia. In a specific embodiment, the neuronal cell is, for example, a nociceptive dorsal root ganglion neuron.

In another embodiment, the cell is a glial cell, e.g., an astrocyte, oligodendrocyte or a Schwann cell.

In another embodiment, the methods further comprises contacting the immortalized cell with an agent that causes differentiation and/or axon elongation. In specific embodiments, the agent cyclic AMP or an analog thereof or an agent that increases intracellular cAMP levels. In a specific embodiment, the cAMP analog is forskolin.

In another aspect, the invention provides methods of producing immortalized neuronal cells comprising introducing a DNA segment encoding an oncogene into a neuronal cell, selecting for neuronal cells that contain the DNA segment, introducing hTERT into the selected cells, and selecting for cells that contain hTERT, thereby producing immortalized neuronal cells.

In one embodiment, the DNA segment is contained in a plasmid. In another embodiment, the hTERT is contained in a plasmid.

In another embodiment, the neuronal cells are selected from a group consisting of neuronal cells from the brain, neuronal cells from the spinal cord, dorsal root sensory ganglia, dorsal root ganglia neuron and autonomic ganglia. In a specific embodiment, the neuronal cell is, for example, a nociceptive dorsal root ganglion neuron.

In another embodiment, the oncogene is selected from the group consisting of Ras, Myc, Raf, and large T-Antigen. In one particular embodiment, the oncogene is the large T-antigen, e.g., the SV40 large T-antigen.

In another embodiment, the hTERT is contained in a plasmid.

In another embodiment, the methods further comprises contacting the immortalized cell with an agent that causes differentiation. In specific embodiments, the agent cyclic AMP, an analog thereof, or an agent that increases intracellular cAMP levels. In a specific embodiment, the cAMP analog is forskolin. In a related embodiment, the forskolin allows the immortalized neurons to differentiate and extend axons.

In another embodiment, the immortalized nociceptive dorsal root ganglion neurons maintain the biochemical and electrophysiological properties of primary neurons. In a related embodiment, the nociceptive dorsal root ganglion neurons express a capsaicin receptor, TRPV1, GDNF-receptor, NGF-receptor, or a sodium channel. In a specific embodiment, the nociceptive dorsal root ganglion neurons express capsaicin receptor TRPV1. In another related embodiment, the nociceptive dorsal root ganglion neurons respond to capsaicin by elevating intracellular calcium flux or generate action potentials when polarized.

In another embodiment, the immortalized nociceptive dorsal root ganglion neurons express one or more axonal markers, e.g., neurofilament or βIII tubulin.

In another aspect, the invention provides methods of producing immortalized dorsal root ganglion neuronal cell line comprising, introducing a plasmid comprising an SV40 large T-antigen into dorsal root ganglion cell, selecting dorsal root ganglion cells that contain the plasmid, introducing hTERT into the selected cells, and selecting for cells that contain hTERT, thereby producing immortalized dorsal root ganglion neuronal line.

In a related embodiment, hTERT is contained in a plasmid.

In another aspect, the invention provides immortalized nociceptive dorsal root ganglion neurons.

In another embodiment, the immortalized nociceptive dorsal root ganglion neurons maintain the biochemical and electrophysiological properties of primary neurons. In a related embodiment, the nociceptive dorsal root ganglion neurons express a capsaicin receptor, TRPV1, GDNF-receptor, NGF-receptor, or a sodium channel. In a specific embodiment, the nociceptive dorsal root ganglion neurons express capsaicin receptor TRPV1. In another related embodiment, the nociceptive dorsal root ganglion neurons respond to capsaicin by elevating intracellular calcium flux or generate action potentials when polarized.

In a specific embodiment, the invention provides immortalized nociceptive dorsal root ganglion neurons comprising an oncogene and hTERT. In exemplary embodiments, the oncogene is selected from the group consisting of Ras, Myc, Raf, and large T-Antigen. In one particular embodiment, the oncogene is the large T-antigen, e.g., the SV40 large T-antigen.

The invention further provides methods for screening for modulators of neuronal cells. These modulators are useful in, for example, the treatment and prevention of pain. In one embodiment, the invention provides high throughput methods of screening using the immortalized cells produced by the methods of the invention.

DETAILED DESCRIPTION OF THE INVENTION

Figures 1A, 1B, 1C, 1D, 1E:
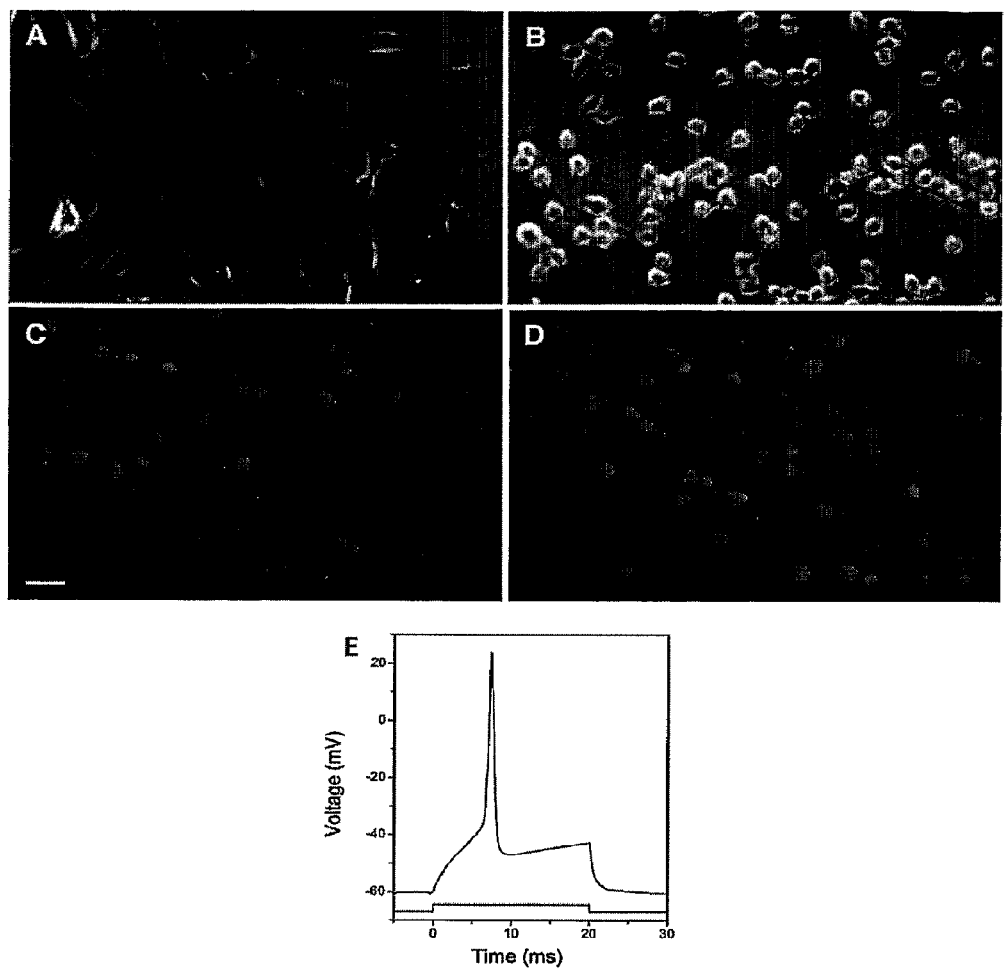
FIGS. 1A to 1E depict immortalized DRG neuronal cells extend neurites, express neuronal markers and generate action potentials after differentiation. Phase contrast images of undifferentiated (FIG. 1A) and differentiated (FIG. 1B) 50B11 cells show extension of axons 4 hours after differentiation with forskolin. After differentiation, 50B11 cells stain with anti-neurofilament (FIG. 1C) and anti-βIII-tubulin antibodies (FIG. 1D). DAPI counterstain shows nuclei. Scale bar=20 μm. A representative action potential is seen in a differentiated 50B11 cell after application of a depolarizing current (FIG. 1E).

To obtain immortalized cells, e.g., dorsal root ganglion cells, the inventors developed a method that reproducibly yields clonal lines of cells, e.g., dorsal root ganglion cells, by introducing an oncogene and hTERT into the cells.

The methods of the invention are particularly useful in creating immortalized cells from cells that are known to be difficult to immortalize. Specifically, the methods of the invention can be used with any cell type, but are particularly useful in cells that have been historically difficult to immortalize, e.g., neuronal cells.

As used herein, the term "vector" refers to a polynucleotide construct designed for transduction/transfection of one or more cell types including for example, "expression vectors" which are designed for expression of a nucleotide sequence in a host cell, such as a neuronal cell.

The terms "polynucleotide" and "nucleic acid", used interchangeably, herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—NH2) or a mixed phosphoramidate-phosphodiester oligomer. Peyrottes et al. (1996) Nucleic Acids Res. 24: 1841-8; Chaturvedi et al. (1996) Nucleic Acids Res. 24: 2318-23; Schultz et al. (1996) Nucleic Acids Res. 24: 2966-73. A phosphorothioate linkage can be used in place of a phosphodiester linkage. Braun et al. (1988) J. Immunol. 141: 2084-9; Latimer et al. (1995) Molec. Immunol. 32:1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The term "oncogene" as used herein is intended to mean a gene whose action promotes cell proliferation. Oncogenes are altered forms of proto-oncogenes and are often expressed in cancerous cells. Exemplary oncogenes include large T antigen, myc, abl, ras, and raf.

"Schwann cell" is a cell of neural crest origin that forms a continuous envelope around each peripheral nerves fiber in situ. A Schwann cell can be identified by detecting the presence of one or more markers of Schwann cell such as glial fibrillar acidic protein (GFAP), protein S100, laminin, or nerve growth factor (NGF) receptor, e.g., using antibodies against these markers. Furthermore, Schwann cells have a characteristic morphology that can be detected by microscopic examination of cultures thereof.

"Immortalized cell line" as used herein means a cell line that can replicate and be maintained indefinitely in in vitro cultures under conditions that promote growth, preferably at least over a period of a year or years.

"Cell line" as used herein is a population or mixture of cells of common origin growing together after several passages in vitro. By growing together in the same medium and culture conditions, the cells of the cell line share the characteristics of generally similar growth rates, temperature, gas phase, nutritional and surface requirements. The cell line can become more homogenous with successive passages and selection for specific traits. Clonal cells are those which are descended from a single cell. A cloned cell culture is a cell culture derived from a single cell. Immortalized cell lines are cells that have been modified to undergo indefinite numbers of successive passages.

A SV40 Large T Antigen (SV-40 LTA) oncogene is intended to encompass any nucleotide sequence which encodes a protein having the function of polyoma (or SV-40) LTa and which is capable of being expressed in the host cell, e.g., a neuronal cell.

The term "hTERT" as used herein is an abbreviation for the human telomerase reverse transcriptase, i.e., the catalytic protein component of human telomerase. hTERT is described in Cong, Y. S., et al. (1999) Hum. Mol. Genet. 8 (1), 137-142 and can be found in GenBank as Accession Number AAD12057. Although human TERT is exemplified herein, one of skill in the art will recognize that TERT molecules from other species, or variants of human TERT that maintain the biological function of hTERT are useful in the methods of the invention.

The human telomerase catalytic subunit has been cloned (see Nakamura, et al. (1997) Science 277: 955; Mayerson, et al. (1997) Cell 90: 78; and Kilian, et al. (1997) Hum Mol Genet 6: 2011; U.S. Pat. No. 6,166,178). Sources of the coding sequence for the human telomerase subunit include any cells that demonstrate telomerase activity such as immortal cell lines, tumor tissues, germ cells, proliferating stem or progenitor cells, and activated lymphocytes. The nucleic acid can be obtained using methods known in the art.

As used herein, the term "pain" is art recognized and includes a bodily sensation elicited by noxious chemical, mechanical, or thermal stimuli, in a subject, e.g., a mammal such as a human. The term "pain" includes chronic pain, such as lower back pain; pain due to arthritis, e.g., osteoarthritis; joint pain, e.g., knee pain or carpal tunnel syndrome; myofascial pain, and neuropathic pain. The term "pain" further includes acute pain, such as pain associated with muscle strains and sprains; tooth pain; headaches; pain associated with surgery; or pain associated with various forms of tissue injury, e.g., inflammation, infection, and ischemia.

As used herein, the term "pain disorder" includes a disease, disorder or condition associated with or caused by pain. Examples of pain disorders include arthritis, allodynia, a typical trigeminal neuralgia, trigeminal neuralgia, somatoform disorder, hypoesthesis, hypealgesia, neuralgia, heuritis, neurogenic pain, analgesia, anesthesia dolorosa, causlagia, sciatic nerve pain disorder, degenerative joint disorder, fibromyalgia, visceral disease, chronic pain disorders, migraine/headache pain, chronic fatigue syndrome, complex regional pain syndrome, neurodystrophy, plantar fasciitis or pain associated with cancer.

The term pain disorder, as used herein, also includes conditions or disorders which are secondary to disorders such as chronic pain and/or neuropathic pain, i.e., are influenced or caused by a disorder such as chronic pain and/or neuropathic pain. Examples of such conditions include, vasodialation, and hypotension; conditions which are behavioral, e.g., alcohol dependence (see, e.g., Hungund and Basavarajappa, (2000) Alcohol and Alcoholism 35:126-133); or conditions in which detrimental effect(s) are the result of separate disorders or injuries, e.g., spinal cord injuries.

The methods of the instant invention rely on the introduction of two DNA segments, i.e., genes, into a cell which results in the formation of an immortalized cell. These cells can be further differentiated by the addition of a differentiating agent. Importantly, the methods of the invention rely on the incorporation of an oncogene and hTERT into a cell, but the method of introducing these genes into the cell are of secondary importance.

The manner in which the oncogene or hTERT coding region is introduced into the cells of interest is not critical, as long as a functional polypeptide is expressed. Expression can be extrachromosomal or following integration into the celluluar genome. Any of a variety of techniques can be used to introduce the oncogene or the hTERT gene into the desired cells, including electroporation, liposomes, or viral vectors. See Molecular Cloning, $3^{rd}$ Edition, 2001, by Sambrook and Russell. In one embodiment, the coding sequence is introduced using a viral vector, for example SV40, adenovirus, Herpes simplex virus, adeno-associated virus, and the like. See Blomer et al., Human Molecular Genetics 5 Spec No: 1397-404, 1996; Zern et al., Gene Ther. 6: 114-120, 1999; and Robbins et al., Trends in Biotechnology 16: 35-40, 1998.

A specific means for incorporating the hTERT coding region into the cells of interest is to use a recombinant retrovirus that provides for integratration of the DNA segment efficiently and stably into the genome of the target cell.

The retroviral vectors generally include as operatively linked components, retroviral long terminal repeats, packaging sequences and cloning site(s) for insertion of heterologous sequences. Other operatively linked components may include a nonretroviral promoter/enhancer and a selectable marker gene. Examples of retrovirus expression vectors which can be used include DC-T5T (Sullenger et al. 1990. Mol. Cell Biol. 10: 6512-65230), kat (Blood. 1994 83: 43-50), BOSC (Proc. Natl. Acad. Sci. (USA) (1993) 90: 8392-8396), pBabe (Proc. Natl. Acad. Sci. (USA) (1995) 92: 9146-9150) and RetroXpreSS™ (Clontech, Palo Alto, Calif.). An expression vector is available that includes the hTERT gene, for example pBabe-puro-hTERT (Morgenstern and Land 1990). In some instances, it may be desirable to increase expression of the hTERT gene by utilizing other promoters and/or enhancers in place of the promoter and/or enhancers provided in the expression vector. These promoters in combination with enhancers can be constitutive or regulatable. Any promoter/enhancer system functional in the target cell can be used. (See for example, Molecular Virology pp. 176-177; Hofmann, et al. 1996. Proc. Natl. Acad. Sci. (USA) 93: 5185-5190; Coffin and Varmus, 1996. Retroviruses. Cold Spring Harbor Press, NY; Ausubel et al. 1994. Current Protocols in Molecular Biology. Greene Publishing Associates, Inc. & Wiley and Sons, Inc.). Examples include: CMV immediate-early promoter, SV40, thymidine kinase promoter, metalothionine promoter, and tetracycline operator (Hofman et al., (1996) Proc. Natl. Acad. Sci (USA) 93: 5185-5190).

For transfection, the neuronal cells or other cells to be transfected are suspended in a suitable culture medium containing recombinant retrovirus vector particles. Many different suitable culture media are commercially available. They include DMEM, IMDM, and .alpha.-MEM, with 5-30% serum and often further supplemented with, e.g., BSA, one or more antibiotics and optionally growth factors suitable for stimulating cell division. Recombinant retrovirus vector particles are harvested into this medium by incubating the virus-producing cells in this medium. To enhance gene transfer, compounds such as polybrene, protamine sulphate, or protamine HCl generally are added. Usually, the cultures are maintained for 2-4 days and the recombinant retrovirus vector containing medium is refreshed daily. Optionally, the cells to be transfected are precultured in medium with growth factors but without recombinant retrovirus vector particles for up to 2 days, before adding the recombinant retrovirus vector containing medium. For successful gene transfer it is essential that the target cells undergo replication in culture. It is often beneficial to transform, transfect, or electroporate a number of times to obtain a higher number of cells containing the desired DNA segment. To maximize the number of cells containing the desired DNA segment, the cells are transformed, transfected, or electroporated and allowed to recover for a number of hours or days and then transformed, transfected, or electroporated again. This process may be repeated 2, 3, 4, 5, 6 or more times in order to maximize the number of cells containing the desired DNA. After the final cycle is performed, cells containing the desired DNA are selected using methods that are routine in the art.

In exemplified embodiments, the oncogene and hTERT are introduced into the cell by electroporation. After one or more rounds of electroporation, cells containing the oncogene are selected using an antibiotic resistance marker introduced into the cell along with the oncogene. Once cells containing the oncogene are selected, hTERT is introduced by electroporation. After one or more rounds of electroporation, cells containing hTERT are selected. The selected cells contain both the oncogene and hTERT.

Once cells containing an oncogene and hTERT are selected, the cells can be differentiated by exposing the cells to differentiation agent. In the case of neuronal cells, this agent can be cAMP, a cyclic AMP analog, or a substance that increases intracellular levels of cAMP. Exemplary cAMP analogs are 8-pCPT-2'-O-Me-cAMP, 8Br-cAMP, Sp-cAMPS, and forskolin. In one exemplified embodiment, the agent is forskolin.

The immortalized cells produced by the methods described herein are particularly useful in screening assays. Specifically, the cells produced by the methods of the instant invention are ideal for high throughput screening. In a specific embodiments, the immortalized nociceptive DRG sensory neurons produced by the methods of the invention are ideal for identifying modulators of neuropathic pain. Previous attempts at identifying modulators of neuropathic pain have focused on identifying TRPV1 antagonists. However, TRPV1 has been expressed in non-neuronal cell lines and the calcium flux induced by capsaicin was used as an outcome measure for high throughput screening (HTS) (Garcia-Martinez C et al. (2002) *Proc Natl Acad Sci USA* 99:2374-2379; Gunthorpe M J et al. (2004) *Neuropharmacology* 46:133-149; Masip I et al. (2004) *J Comb Chem* 6:135-141). Although these cells expressing recombinant TRPV1 may be useful, a nociceptive sensory neuronal cell expressing TRPV1 will be more relevant because the non-neuronal cell lines may lack the appropriate intracellular signaling pathways associated with and downstream of TRPV1 in nociceptive sensory neurons. Likewise, neuronal cells from other areas of the body can be immortalized and would be useful for high throughput screening to identify modulators for these cells. For example, sensory, motor or cortical neurons can be immortalized and used to identify modulators of, for example, Alzheimer's disease, Parkinson's disease, Huntington's disease, multiple sclerosis, or amyotrophic lateral sclerosis (ALS).

Accordingly, the instant invention provides methods of screening for modulators of human cells, e.g., human neuronal cells, by contacting an immortalized cell of the invention with a candidate modulator and determining if the modulator has a desired biological effect, e.g., binding to and/or modulating the activity of TRPV1.

In a specific embodiment, the invention provides screening methods using the immortalized nociceptive DRG neurons produced by the methods of the invention to identify modulators of pain, e.g., neuropathic pain. Immortalized nociceptive DRG neurons are contacted with candidate modulators and the ability to modulate, for example, capsaicin induced toxicity can be monitored to determine if a candidate modulator is a modulator of neuropathic pain.

The invention provides methods (also referred to herein as "screening assays") for identifying modulators, i.e., candidate or test compounds or agents (e.g., peptides, peptidomimetics, small molecules, ribozymes, or antisense molecules) which bind to bind to and/or modulate the activity of the immortalized cells of the invnetion. Compounds identified using the assays described herein may be useful for treating pain disorders.

Candidate/test compounds include, for example, 1) peptides such as soluble peptides, including Ig-tailed fusion peptides and members of random peptide libraries (see, e.g., Lam, K. S. et al. (1991) Nature 354:82-84; Houghten, R. et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

Candidate modulators can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) Anticancer Drug Des. 12:145).

Examples of methods for the synthesis of molecular libraries can be found in the art, for example in DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233. Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. 97:6378-6382); (Felici (1991) J. Mol. Biol. 222:301-310.

Alternatively, test compounds can be designed based on the structure of known modulators of pain, or compounds that are know to bind to receptors expressed by neurons.

The ability of a given modulating agent to modulate pain can be quantitated by using any one of the following tests: tight ligation of L6 and L7, as a model of neuropathic pain; complete Freund's adjuvant into knee joint or hind paw as a model of Long term inflammatory pain (Palecek, J. (1992) Neurophysiol 68:1951-66); nerve ligation (CCI); thermal hyperalgesia, tactile allodynia and cold allodynia (Carlton, S. M. et al. (1994) Pain 56:155-66); thermal paw withdrawal latency (Hargreaves test); von Frey mechanical withdrawal threshold; the hot-plate latency test; the tail flick test (Stone, L. S., et al. (1997) NeruroReport 8:3131-3135); the warm-water immersion tail flick assay (Stone, L. S., et al. (1997) NeruroReport 8:3131-3135); the crush injury to the sciatic nerve test (De Konig, et al. (1986) J. Neurol. Sci. 74:237-246); the cold water allodynia test (Hunter, et al. (1997) Pain 69:317-322; the paw pressure latency assay (Hakki-Onen, S., et al. (2001) Brain Research 900(2):261-7; or the radiant heat test (Yoshimura, M., (2001) Pharm. Research 44(2): 105-11).

Briefly, the tail flick latency test involves projecting a beam of light to the tail of an animal. The time is measured from the onset of the tail heating and stops at the moment of the tail flick. Typically, five tail flick latency (TFL) measurements are made per rat per session with 5-10 minutes between trials.

The preceding paragraphs set forth high throughput screening methods using immortalized nociceptive DRG neurons to identify modulators of neuropathic pain. However, one of skill in the art could adapt these assays to identify modulators of other conditions and immortalized cell lines made using the methods of the invention.

EXAMPLES

It should be appreciated that the invention should not be construed to be limited to the examples that are now described; rather, the invention should be construed to include any and all applications provided herein and all equivalent variations within the skill of the ordinary artisan.

Example 1: Generation and Characterization of DRG Neuronal Cell Line

Materials and Methods

Unless noted otherwise all reagents and materials were purchased from Invitrogen (Carlsbad, Calif.). Animal studies were conducted according to the protocols approved by the institutional Animal Care and Use Committee.

Construction of SV40 Large T-Antigen and hTERT Expression Vectors

For cloning of the SV40 large T-antigen, plasmid construct pZipSV776-1 was used as the template for PCR amplification of the gene fragment coding for SV40 large T-antigen. PCR reaction was primed by oligonucleotides 5'-CACCGCTTTGCAAAGATGGATAAAG (sense; SEQ ID NO: 1) and 5'-AATTGCATTCATTTTATGTTTCA (antisense; SEQ ID NO: 2). Amplification was performed using the Expend High Fidelity PCR System (Roche, Indianapolis, Ind.). The PCR product was cloned into the pENTR/D-TOPO vector by directional TA-cloning. After confirmation of the sequence, the target SV40 large T-antigen gene was transferred into pLenti6/V5-Dest vector using Gateway technology. In the destination vector, the SV-40 large T-antigen was under the control of $P_{CMV}$, and the selection marker, blasticidin resistance gene, was under the control of $P_{SV40}$. The hTERT expression construct pBabe-hygro-hTERT carrying hygromycin resistant gene (also a kind gift of William C. Hahn at Harvard University), was used to transfer the hTERT gene into the pLenti6N5-Dest vector using Gateway technology. In the destination vector, the hTERT was under the control of $P_{CMV}$, and the selection marker, hygromycin resistance gene, was under the control of $P_{SV40}$. The expression plasmids were prepared and purified using Plasmid MIDI Kit (Qiagen, Valencia, Calif.). Endotoxin-free plasmid was suspended in distilled water for electroporation.

Electroporation into Dissociated DRG Neurons and Selection of Clones

Dissociated primary DRG neuronal cells were prepared as previously described (Hoke A et al. (2003) J Neurosci 23:561-567; Keswani S C et al. (2003) Ann Neurol 53:57-64) and the plasmid was electroporated. Approximately $5 \times 10^4$ cells in 90 ml Opti-MEM media were mixed with 10 ml plasmid (1 mg/ml) and transferred into a 0.2 cm Gene Pulser cuvette (Bio-Rad, Hercules, Calif.). After 10 minutes of incubation at room temperature, a single square-wave pulse (100 V, 950 mF, ~40 ms) was delivered by a Gene Pulser II with a Capacitance Extender Plus (Bio-Rad, Hercules, Calif.). Culture medium at 4° C. was immediately added to the cells and the cuvette was kept on ice for 10 minutes. Cells were plated in T75 flasks in culture medium without antibiotics (Neurobasal medium, 10% FBS, 0.5 mM glutamine, 1×B-27 supplement, 0.2% glucose). In order to increase the efficiency of electroporation and incorporation of large T-antigen into terminally differentiated sensory neurons, the process of electroporation was repeated 3-4 times before addition of antibiotic selection media. About 60-70% of the cells survived the electroporation process. Twenty-four hours after the last electroporation, culture medium was replaced by selection medium containing blasticidin (5 μg/ml) and cells were maintained in this medium for 1-2 weeks until isolated colonies with 200-300 cells formed. Colonies were picked and expanded using standard culture methods when reached 80-90% confluence. For hTERT transduction, SV-40 transfected and blasticidin resistant cells were trypsinized and electroporated with the hTERT plasmid as above for the large T-antigen. The electroporation was repeated 3-4 times. About 60-70% of the cells survived the electroporation process. Twenty-four hours after the last electroporation, culture medium was replaced by selection medium containing hygromycin (50 mg/ml) and cells were maintained in this medium for 1-2 weeks until isolated colonies with 200-300 cells formed. Colonies were picked and expanded using standard culture methods when reached 80-90% confluence.

Induction of Neuronal Differentiation and Characterization of the Immortalized Neuronal Clone One of the immortalized DRG neuronal cell lines (50B11) maintained self-replication capability over many cell divisions (>300) and was used in further analysis of neuronal properties. Differentiation and axonal elongation was induced in these cells by addition of forskolin (50 μM) into the culture medium. Within hours, more than 90% cells stopped dividing and extended long neurites. These cells were grown in 24-well plates on glass coverslips, fixed with 4% paraformaldehyde and immunostained for presence of neurofilament (SMI-32 antibody from Sternberger Monoclonals Inc., Lutherville, Md.), βIII-tubulin (Promega, Madison Wis.), transient receptor potential channel, vanilloid subfamily member-1 (TRPV-1) (Abeam, Cambridge, Mass.), calcitonin gene related protein (CGRP) (source, city, state) or isolectin B-4 (IB4) (Vector Laboratories, Burlingame, Calif.) using standard methods (Keswani et al., supra). Slides were counterstained with 4',6-Diamidino-2-phenylindole (DAPI) and mounted with Vectashield (Vector Laboratories, Burlingame, Calif.). Specificity of all primary and secondary antibodies was confirmed using appropriate positive and negative control cultures.

The electrophysiological recording techniques employed were similar to those described by Hamill et al. (Hamill O P et al. (1981) *Pflugers Arch* 391:85-100). The external solution contained (mM) 145 NaCl, 5 KCl, 2 $CaCl_2$, 1 $MgCl_2$, 10 D-glucose and 10 N-2-hydroxyethylpiperazine-Np-2-ethanesulfonic acid (HEPES) (pH 7.4; 310-320 mOsmol.) Cells were continuously superfused at 2-3 ml/min. Using the whole-cell patch-clamp technique, data were obtained with borosilicate thin-walled micropipettes (BORO, BF150-110-10, Sutter, Novato, Calif.) made with a Flaming-Brown Puller (P-87, Sutter Instruments, Novato, Calif.). Micropipettes were filled with (in mM) 140 KCL, 1 $CaCl_2$, 1 $MgCl_2$, 10 HEPES, 10 ethyl glycol-bis(3-aminoethyl ether)-N,N,Nρ,Nρ-tetraacetic acid (EGTA), 4 Mg-ATP adjusted to a pH of 7.3 with Tris buffer. Pipette resistances measured 3 to 6 ME. Current-clamp recordings were obtained with an Axopatch 200B amplifier (Axon Instruments Inc. Foster City, Calif.) and data was filtered on-line at 2 kHz. Recordings were made at a holding potential ($V_H$) of −60 mV. For statistical evaluation we used ANOVA (Origin version 6, Microcal Software Inc., Northampton, Mass.)

For analysis of changes in gene expression, 501311 cells were grown in media containing forskolin (50 μM), NGF (10 ng/ml), GDNF (10 ng/ml) or vehicle control for 24 hours. Total RNA was isolated using the TRIzol Reagent according to the manufacturer's recommendation. Two μg total RNA was reverse-transcribed using Ready-To-Go You-Prime First-Strand Bead (Amersham Biosciences, Piscataway, N.J.) according to manufacturer's protocols. Real-time PCR was carried out in a DNA Engine Opticon Continuous Fluorescence Detection System using DyNAmo SYBR Green Polymerase (MJ Research, Waltham, Mass.). All primers were designed according to the individual gene sequence in the GenBank/EMBL nucleotide sequence database (primer sequences are available upon request). The binding positions of all primers were chosen to produce amplicons of 150 to 200 base pairs and to achieve maximum efficiency and specificity. All primer sequences were checked for specificity by a BLAST search in the GenBank/EMBL nucleotide sequence database. The primers were synthesized by Integrated DNA Technologies, Inc. (Coralville, Iowa). The amplification of internal control housekeeping gene, GAPDH, was carried out using a commercial kit (Applied Biosystems, Foster City, Calif.) according to the protocol supplied by the manufacturer. The expression levels of individual genes before and after treatment were calculated using the comparative $C_T$ method.

$Ca^{2+}$ microfluorimetry and imaging in forskolin-differentiated 50HB cells were performed by ratiometric imaging of the Ca2+-sensitive fluorescent dye fura-2. Cells were grown on glass coverslips in 12-well dishes and calcium imaging was done with and without differentiation with 50-μM forskolin. Cell were loaded for 15 min at 37° C. with 2 M fura-2 acetoxymethyl ester (Molecular Probes, Carlsbad, Calif.) in Krebs-HEPES buffer (100 mM NaCl, 2.0 mM KCl, 1.0 mM CaCl2, 1.0 mM MgCl2, 1.0 mM NaH2PO4, 4.2 mM NaHCO3, 12.5 mM HEPES and 10.0 mM glucose), then washed for 3 times in buffer to remove remaining fura-2 ester. The coverslip with loaded cells was then mounted on an inverted epifluorescence microscope (Zeiss, Axiovert 200) and covered with 60 μl Krebs-HEPES buffer or buffer with capsaicin. In capsazepin pretreatment experiments, capsazepin was added Images were acquired every ~3 seconds with an extended Hamamatsu Digital Camera C4742-95 (Hamamatsu Photonics, Barcelona, Spain) using a dual filter wheel (Sutter Instruments, Novato, Calif., USA) equipped with 340 and 380 nm, 10-nm-bandpass filters (Omega Optics, Madrid, Spain). Data was acquired using InCyt Im2 software (Intracellular Imaging, Inc.). Fluorescence changes are expressed as the ratio of fluorescence at 340 and 380 nm ($F_{340}/F_{380}$).

Neuronal Toxicity Assays

Conditions for culturing the 50B11 cells and measuring the ATP levels were optimized for the 96-well plate format. Initially 500 cells/well were plated in 96-well plates for 24 hours and then differentiated with forskolin (50 µM) in culture medium with reduced serum (0.2%). Varying concentrations of ddC with or without immunophilin ligand GPI-1046 were added to the wells for another 24 hours. Cellular ATP levels were measured using the ViaLight Plus kit (Cambrex, city, state) according to manufacturer's instructions. This luciferase-based assay allows measurement of ATP levels on a luminometer with minimal manipulation of the well contents.

Measurements of axonal lengths to determine axonal degeneration induced by ddC were done as described before (Keswani et al., supra). Briefly, DRG cultures were prepared from embryonic E14.5 rats, plated onto collagen coated glass coverslips and allowed to extend axons for 48 hours. Then ddC, GPI-1046 or vehicle controls were added to the media for another 24 hours. Cells were fixed and stained with anti-ßIII-tubulin antibody to delineate the axons. Axon length measurements were done in multiple fields using a random sampling method. Each experiment was done in triplicates and repeated at least twice. Statistical analysis was done using ANOVA with correction for multiple comparisons.

Results

Immortalized DRG Neuronal Cells Extend Neurites, Express Neuronal Markers and Generate Action Potentials after Differentiation One of the clones generated after immortalization was further studied after evaluation using the initial screening of neurite extension in response to forskolin. This clone, 50B11, stopped dividing immediately after addition of forskolin and within 4 hours extended neurites at least twice as long as the neuronal body diameter (FIGS. 1A and 1B). Within 24 hours of differentiation, the cells were positive for neuronal markers ßIII-tubulin and neurofilament (FIGS. 1C and 1D). We studied these cells before and after differentiation using patch clamping. Data were obtained from a total of 14 cells (8 undifferentiated cells and 6 differentiated cells). Collectively these cells displayed a mean resting membrane potential of −57.9±2.1 mV. There were no statistically significant differences between the mean resting potential values of the undifferentiated and differentiated groups (−57.4±1.9 mV versus −58.3±2.7 mV, mean±SEM; ANOVA, P>0.05). No spontaneous activity, either synaptic or action potential discharge, was observed when differentiated or undifferentiated cells were held at their resting membrane potential for periods up to 10 min. Electrical stimulation of undifferentiated cells with depolarizing current steps did not induce an action potential (n=0/8). On the other hand, when differentiated cells were stimulated, action potentials could be elicited (n=5/6; FIG. 1E).

50B11 Neuronal Line Express Markers of Small Diameter Sensory Neurons

Figures 2A, 2B, 2C:
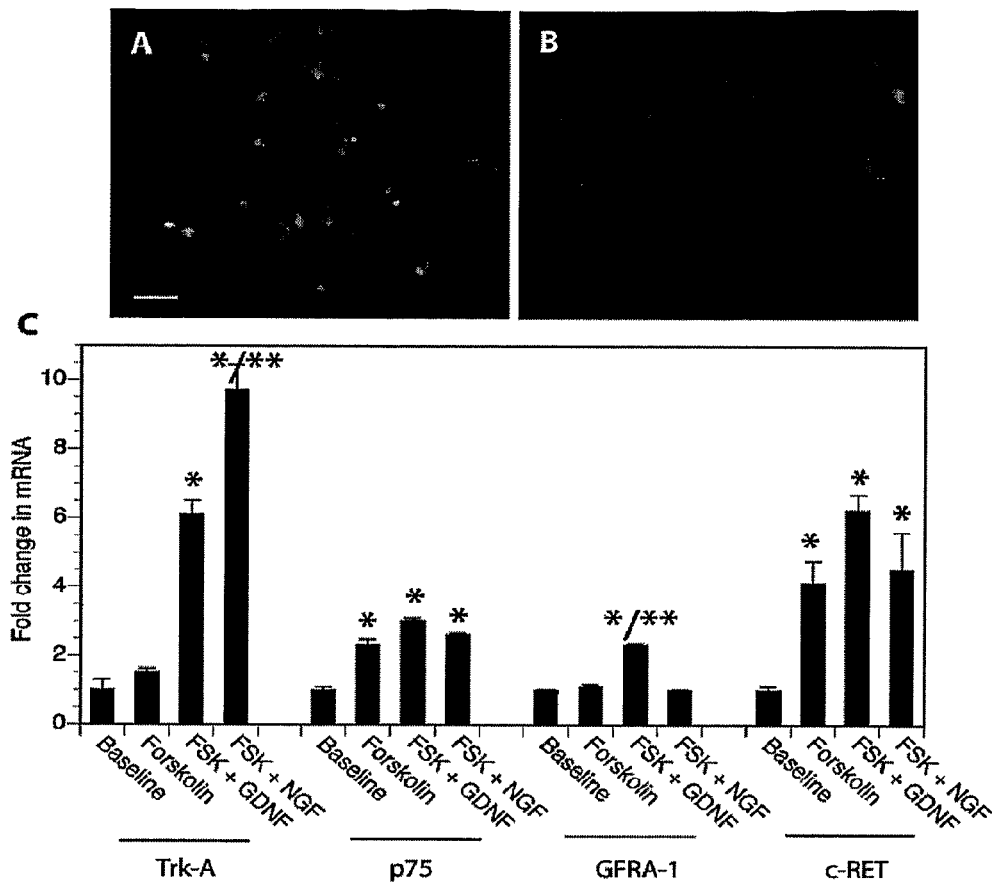
FIGS. 2A-C depict 50B11 neuronal line expresses markers of small diameter sensory neurons. Immunofluorescence images of 50B11 cells stained with fluorescently tagged IB4 (A) and anti-CGRP (B). Nuclei are counterstained with DAPI. Scale bar=20 μm. Changes in expression of mRNA for p75, Trk-A, c-ret and GFRα-1 in the presence of forskolin (FSK), NGF and GDNF compared to baseline levels of undifferentiated 50B11 cells (C). (n=6-8/group; error bars denote standard error of mean; *=p<0.05 compared to baseline; **=p<0.05 FSK+GDNF versus FSK+NGF)

Small diameter DRG sensory neurons are generally divided into two categories; peptidergic ones with dependence on NGF, and non-peptidergic ones with dependence on GDNF (Bennett D L et al. (1998) *J Neurosci* 18:3059-3072). Markers such as CGRP for peptidergic neurons and IB4 for non-peptidergic neurons can identify these subgroups of small diameter sensory neurons. The 50B11 line expressed both markers when differentiated in the presence of forskolin (FIGS. 2A and 2B). Furthermore, 50B11 cells expressed receptors for NGF (low affinity NGF receptor p75 and high affinity Trk-A) and GDNF (c-ret and GDNF family receptor alpha-1, GFRα-1) and upregulated these receptors when differentiated with forskolin (FIG. 2C). Interestingly, the upregulation of receptors was neurotrophic factor specific; NGF receptor, Trk-A was more upregulated in the presence of NGF compared to GDNF and similarly GDNF receptor, GFRα-1 was more upregulated in the presence of GDNF compared to NGF.

50B11 Neuronal Line Express Nociceptive Markers and Respond to Capsaicin

Figures 3A, 3B, 3C:
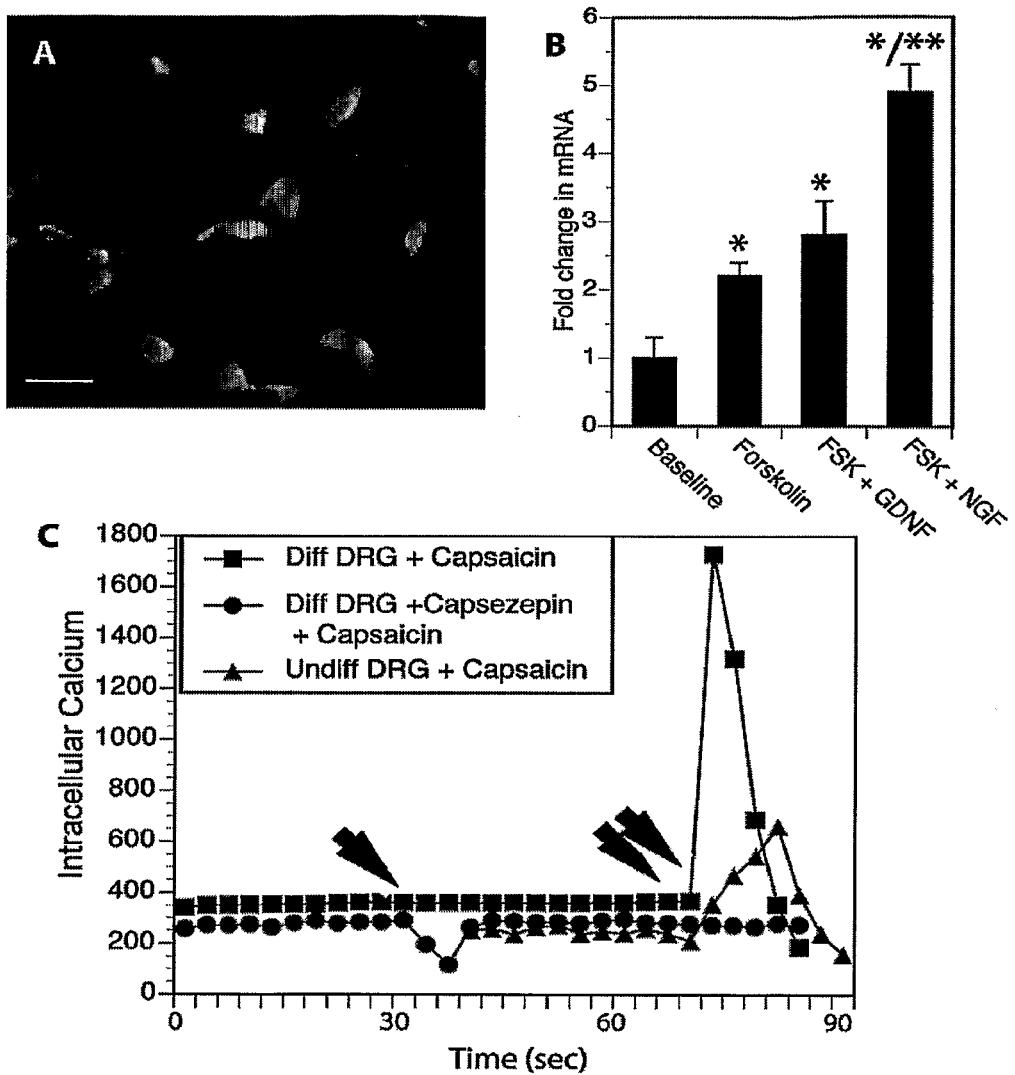
FIGS. 3A-C depict 50B11 neuronal line expresses nociceptive markers and respond to capsaicin. Immunofluorescence image of 50B11 cells stained with anti-TRPV-1 antibody (A). Nuclei are counterstained with DAPI. Scale bar=25 jam. Fold change in TRPV-1 mRNA in response to differentiation and neurotrophic factor treatment is seen (B). (n=6-8/group; error bars denote standard error of mean; *=p<0.05 compared to baseline; **=p<0.05 FSK+GDNF versus FSK+NGF) Measurements of intracellular calcium levels of undifferentiated 50B11 with vehicle control treatment (red line), after differentiation with forskolin with (green) and without (blue) capsazepin pretreatment (C). Single arrow indicate the time at which capsazepin was added and double arrows indicate the time at which capsaicin was added.

Once we determined that the 50B11 line had small diameter sensory neuronal markers, we explored the possibility that it was a nociceptive neuron. The cells expressed capsaicin receptor TRPV-1 and upregulated their expression when differentiated with forskolin with and without neurotrophic factor treatment (FIG. 3). Furthermore, the 50B11 cells responded to capsaicin with a rapid rise in intracellular calcium levels. This effect of capsaicin on the 50B11 cells was preventable by pretreatment of the cells with capsazepin, a specific blocker of TRPV-1, suggesting that the effect of capsaicin was mediated through TRPV-1. A graph representative of multiple intracellular calcium measurements is shown FIG. 3C.

Figures 4A, 4B:
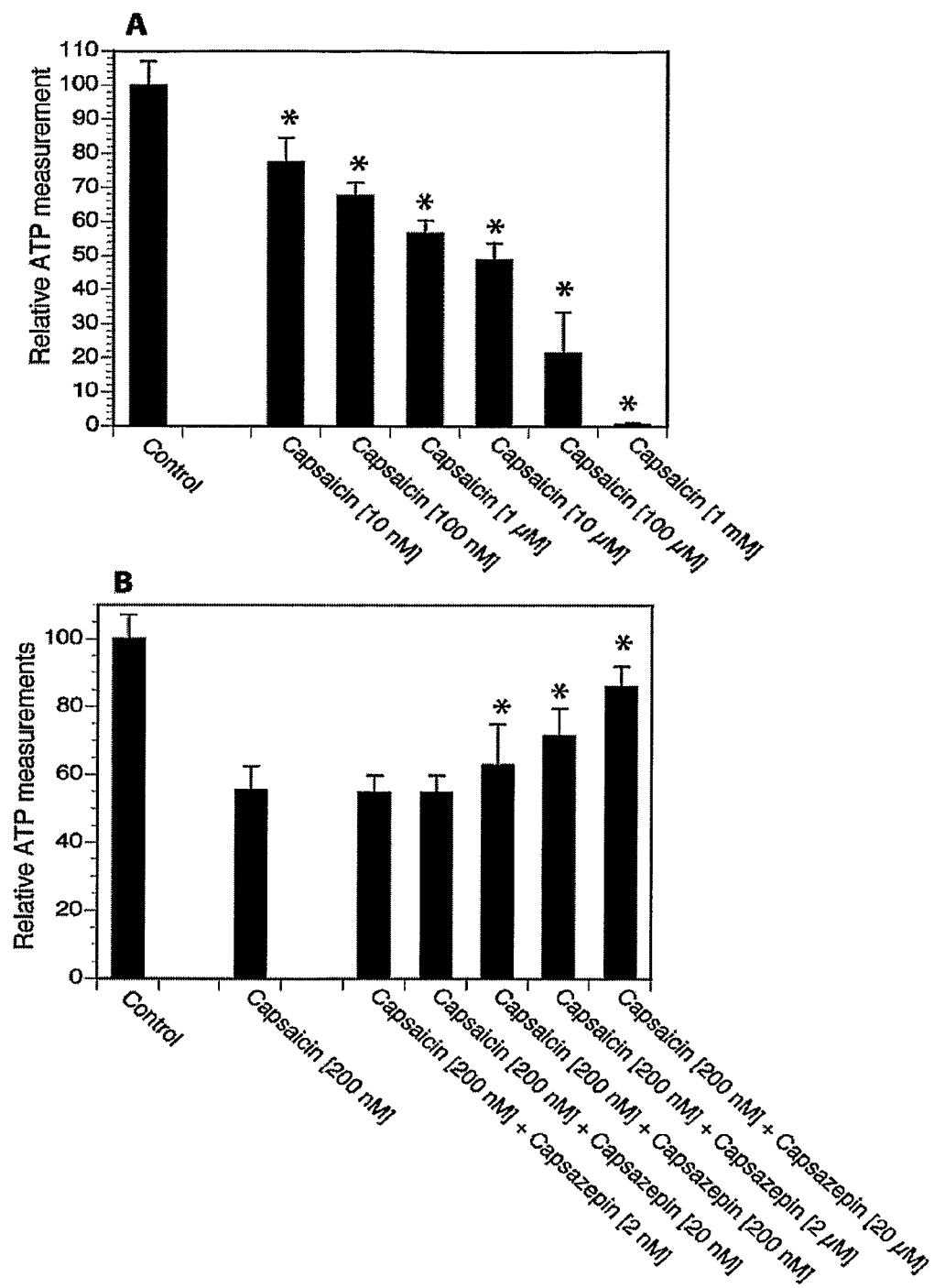
FIGS. 4A-B depict Capsaicin induced neurotoxicity. 50B11 cells were grown in 96-well plates and treated with varying doses of capsaicin (A) and capsaicin plus capsazepin (B) for 24 hours; cellular ATP levels were measured and expressed as a percentage of control cultures. (n=8/condition, error bars denote standard error of mean, *=p<0.05 compared to controls)

Next, we tested whether we can evaluate the neurotoxicity of capsaicin in an assay suitable for 96-well plate format. Capsaicin causes axonal degeneration and death of nociceptive DRG sensory neurons [ref here]. In order to evaluate cell survival we used a luciferase-based assay to measure cellular ATP levels. We first optimized the assay by measuring ATP levels in different numbers of cells grown in the 96-well plates and found that the optimum number of cells for neurotoxicity assays was between 500 and 1000 cells per well. We also optimized the culture conditions and found that low serum levels of 0.2% fetal bovine serum provided the most reliable results (data not shown). We then examined the dose-response curve of capsaicin and found that 10 µM of capsaicin caused about 50% reduction in ATP levels (FIG. 4A); similar to the dose required for neurotoxicity of capsaicin in primary DRG neurons. The capsaicin-induced neurotoxicity was preventable by co-administration of TRPV-1 blocker capsazepin in a dose-dependent manner (FIG. 4B).

Figures 5A, 5B:
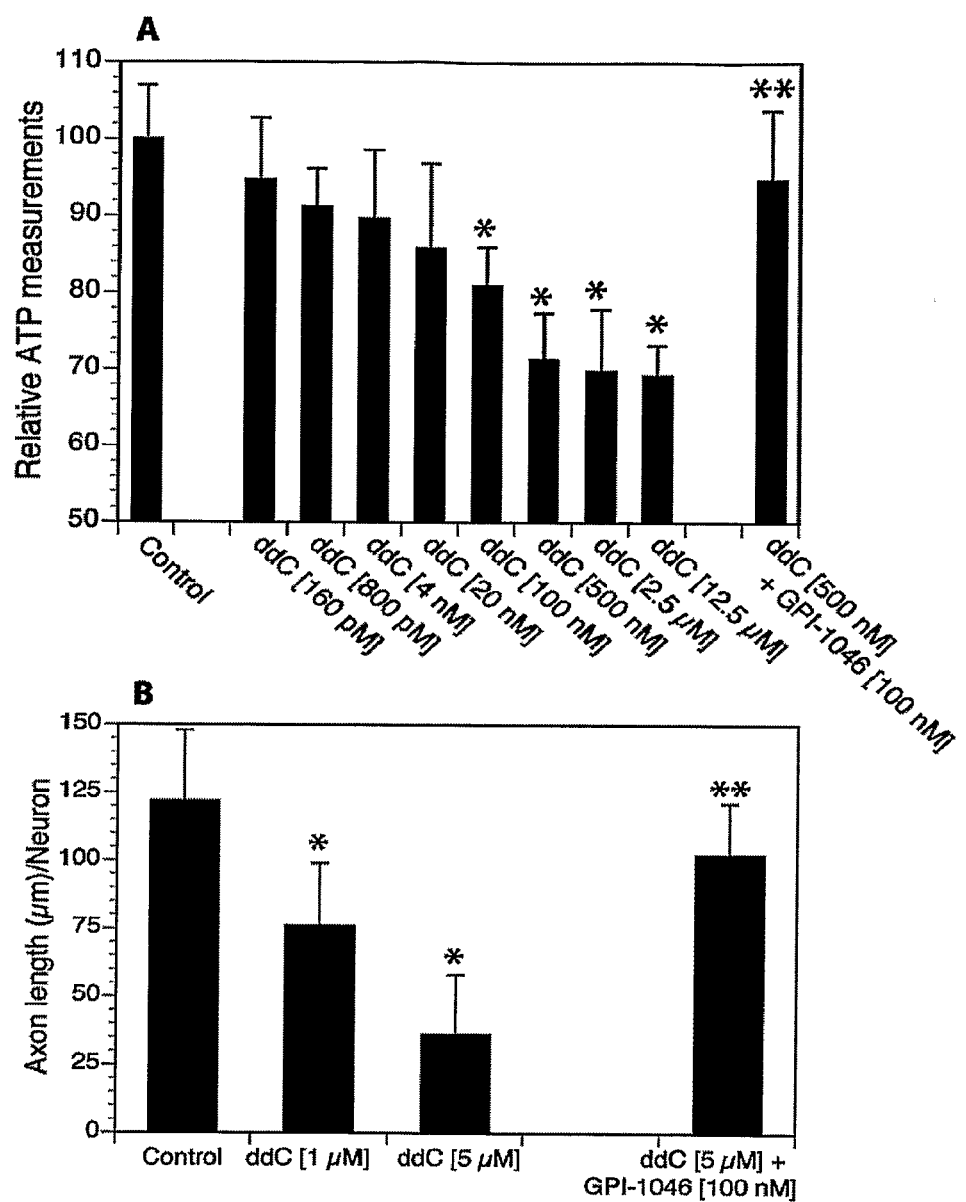
FIGS. 5A-B depict ddC induced neurotoxicity and rescue by GPI-1046. 50B11 cells were grown in 96-well plates and treated with varying doses of ddC and ddC plus GPI-1046 (A) for 24 hours; cellular ATP levels were measured and expressed as a percentage of control cultures. (n=8/condition, error bars denote standard error of mean, *=p<0.05 compared to controls). In validation experiments, 50B11 cells were differentiated and allowed to extend their neurites 24 hours. Then they were treated with ddC or ddC plus GPI-1046 for another 24 hours, and total neurite lengths were measured (B). (n=6/condition, error bars denote standard error of mean, *=p<0.05 compared to controls).

The Immortalized 50B11 Neuronal Line is Suitable for High-Throughout Drug Screening One of the potential uses of 50B11 sensory neuronal line will be their use in high-throughput screening assays. Our laboratory had developed in vitro model of antiretroviral toxic neuropathy using primary DRG sensory neurons (Keswani et al., supra). We adapted this assay to the 50B11 cells and measured cellular ATP levels after varying concentrations of ddC (FIG. 5A). There was a dose-dependent toxicity of ddC at concentrations similar to therapeutic plasma levels in HIV patients. This neurotoxicity was preventable by co-administration of a neuroprotective compound, GPI-1046, a non-immunosuppressive immunophilin ligand. We also validated this toxicity using a more standard measure of axonal degeneration where we differentiated the 50B11 cells, let them extend neurites and then treated them with ddC with and without GPI-1046 for 24 hours and then measured their total neuritic lengths (FIG. 5B).

DISCUSSION

Cellular tools for drug development for peripheral neuropathies and neuropathic pain are limited. We developed a novel method to immortalize nociceptive dorsal root ganglion (DRG) neurons and show that the immortalized DRG neuronal line (50B11) extend neurites when differentiated, express receptors characteristic of small sensory neurons and nociceptive receptor TRPV-1, generate action potentials when depolarized and respond to capsaicin. Furthermore, the cells are easy to grow in large quantities and suitable for high throughput drug screening using in vitro assays for neuropathic pain and peripheral neuropathies.

DRG neurons are terminally differentiated cells that extend long axons to their target tissues. More than half of all DRG neurons are unmyelinated, extend axons to the skin and have nociceptive properties. In many studies on peripheral neuropathies and neuropathic pain, rat or mouse primary DRG neurons are used. However, obtaining these cells in sufficient quantities to perform high-throughput drug screening is nearly impossible. An alternative is to use neuronal cell lines derived from neuroblastomas or immortalized neural crest precursor/stem cell lines (Rao M S and Anderson D J (1997) *J Neurobiol* 32:722-746). However, these approaches have caveats for neuropathic pain research and drug screening. These cells are often heterogeneous and retain the potential to differentiate into multiple neuronal and non-neuronal cell types in a mixed environment. Furthermore, they are not likely to respond to drugs in a consistent manner because of this heterogeneity in culture. In contrast, the nociceptive DRG neuronal cell line that we developed is clonal; therefore, all of the cells are similar to each other and in biological assays behave in a predictable manner. These cells can be grown in large quantities, differentiated into nociceptive neurons that express proper markers and ion channels necessary for nociception and generation of action potentials, and used in high-throughput drug screening.

The immortalized DRG neuronal line, 50B11, was likely to be generated from a nociceptive neuron with potential to differentiate into either a peptidergic neuron with NGF dependency or non-peptidergic neuron with GDNF dependency. During development, all future nociceptive neurons are dependent on NGF and express markers for NGF-dependent neurons (p75 and TrkA) (McMahon S B et al. (1994) *Neuron* 12:1161-1171), but a subgroup switch dependency and express markers of GDNF-dependent neurons such as IB4 (Molliver D C et al. (1997) *Neuron* 19:849-861). The 50B11 line retained this bi-potentiality because in the presence of a given neurotrophic factor, it upregulated the appropriate receptors. Furthermore, the cells extended longer neurites in the presence of either NGF or GDNF.

In order to immortalize rat DRG neurons, we used a two-step transformation process. Although combination of SV-40 large T antigen and hTERT had been used before to immortalize primary airway epithelial cells (Lundberg A S et al. (2002) *Oncogene* 21:4577-4586), this approach had not been applied to generation of immortalized cell lines from terminally differentiated cells such as neurons. In order to increase our transfection efficiency and generation of transformed neurons, we used a different approach and performed multiple electroporations before adding the selection antibiotic to the media. We obtained multiple clones and characterized one in detail. We were able to grow this cell line, 50B11, through multiple doublings (well over 300) without loss of differentiation potential. Stocks of cells from early and late passages had similar properties in terms of their differentiation potential.

Differentiation into neurons with nociceptive properties was accomplished by using forskolin. During development DRG neurons express high levels of cAMP but downregulate it after they are mature and their axons reach the target tissues. Elevated cAMP levels in the DRG line could be accomplished by methods other than forskolin, but we chose forskolin mainly because of ease of use and relatively lower coat compared to other choices such as membrane permeable dibutryl-cAMP (db-cAMP). This is an important issue to consider in designing assays for high-throughput screening. Furthermore, we chose an assay that is also easy to scale up for high-throughput screening. Measurement of cellular ATP levels using the luciferase-based assay is suitable in multiple ways. First, one can use it as a measure of cellular health and cell numbers as ATP levels in cells correlate with the number of healthy cells. Second, the assay is simple to administer with no wash steps involved. It requires addition of reagents into the wells twice, once to lyse the cells and second to add reagents for the luminescence. This improves reproducibility of the assay and will reduce the number of multiplicates needed during drug screening.

In summary we have developed an immortalized DRG sensory neuronal line with nociceptive properties suitable for high-throughput drug screening for peripheral neuropathies and neuropathic pain. The transfection and selection methods we developed can be used to generate other neuronal populations, including neurons from human tissues such as brain, spinal cord, dorsal root sensory ganglia or autonomic ganglia.

Example 2: Generation and Characterization of Human Fetal Astrocytes and Schwann Cells Human astrocytes or Schwann cells were prepared from aborted fetal tissues using standard cell culture techniques. Cells were cultured in Neurobasal media (Neurobasal MEM plus 10% FBS, 0.5 uM glutamin, 2% glucose, 1×B27 supplement) for 3-7 days in an incubator with 5% CO2 at 37° C. Cells were detached with a cell scraper and washed 2 times in Opti-MEM (Invitrogen, CA) and 0.8-1.0×10$^6$ cells were suspended in 100 ul Opti-MEM and dissociated with pipetting using a 200 µl tip.

Five µg pLenti6/V5-DEST plasmid carrying hTERT gene (pLenti6/hTERT) in 1.7 µl TE (pH8.0) and 15 µg pLenti6/V5-DEST plasmid carrying SV40 large T antigen gene (pLenti6/SV40) in 5 µl TE (pH8.0) were mixed with cells, transferred into a 0.2 cm gene-pulser cuvette (Bio-Rad, CA) and incubated for 5 minutes at room temperature. Gene Pulser Xcell Electroporation System (Bio-Rad, CA) was set at 850 µF×90V and the cells were pulsed once (with a time constant of 35-40 mini-second). 500 µl ice-chilled culture media (antibiotics free) was immediately added to the cells and the cuvette was kept on ice for 5 minutes. Cells were then transferred into a 75 cm$^2$ (T75) culture flask and cultured in antibiotics-free Neurobasal media for 3-7 days until 70-80% confluence.

The next 3 electroporations were done with the same procedure, but with different amount of pLenti6/hTERT and pLenti6/SV40. For the second electroporation, 10 µg pLenti6/hTERT (in 3.3 µl TE, pH 8.0) and 10 µg pLenti6/SV40 (in 3.3 µl TE, pH 8.0) were mixed with cells. For the third time electroporation, 15 µg pLenti6/hTERT (in 5 µl TE, pH8.0) and 5 µg pLenti6/SV40 (in 1.7 µl TE, pH8.0) were mixed with cells. For the fourth electroporation, 20 μg pLenti6/hTERT (in 6.6 μl TE, pH8.0) and 2 μg pLenti6/SV40 (in 0.6 μl TE, pH8.0) were mixed with cells.

After the fourth electroporation, cells from each gene-pulser cuvette were transferred into 3 T75 culture flasks and cultured in Neurobasal media containing 5 μg/ml blasticidin (Invitrogen, CA) for 6-8 days. Blasticidin-resistant colonies were detached with 0.05% trypsin, isolated with glass capillary pipettes and transferred into 24 well plates. Cells were then cultured for 5-10 days (depending on the size of the original colony) in blasticidin-containing media and a portion of the cells were plated in a T75 culture flask for further cloning. The resulted colonies were propagated in T75 flasks, stored frozen in freezing media (culture media plus 10% DMSO), and characterized.

The immortalized human astrocyte and Schwann cell lines were further characterized by RT-PCR, immunohistochemistry and Western blotting. Cell lines expressed glial markers such as GFAP, S100, CD44 and tenascin by RT-PCR, and GFAP and S100 by immunohistochemistry. Furthermore, astrocyte line expressed glutamate transporters EAAT-1 and EAAT-2 by RT-PCR and western blotting. Further characterization, including biological assays are ongoing.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for generating an immortalized human cell comprising:
   introducing into a neuronal cell a DNA segment encoding an oncogene by at least two successive electroporation steps wherein each electroporation step is followed by a step of recovery for a number of hours or days;
   selecting for a cell containing the DNA segment; and
   introducing human telomerase reverse transcriptase into the selected cell;
   culturing the selected cell;
   selecting for a cell containing the human telomerase reverse transcriptase;
   thereby generating an immortalized cell.

2. The method of claim 1, wherein the DNA segment is contained in a plasmid.

3. The method of claim 1, wherein human telomerase reverse transcriptase is introduced by a retrovirus.

4. The method of claim 1, wherein the neuronal cell is selected from neuronal cells from the brain, spinal cord, and dorsal root sensory ganglia.

5. The method of claim 1, wherein the human cell is a dorsal root ganglia neuron.

6. The method of claim 5, wherein the dorsal root ganglion neuron is a nociceptive dorsal root ganglion neuron.

7. An immortalized nociceptive dorsal root ganglion neuron made by the method of claim 6, comprising human telomerase reverse transcriptase.

8. The immortalized nociceptive dorsal root ganglion neuron of claim 7, wherein the neuron expresses markers of nociceptive dorsal root ganglion neurons.

9. The method of claim 6, wherein the nociceptive dorsal root ganglion neuron expresses a capsaicin receptor, TRPV1, GDNF-receptor, NGF-receptor, or a sodium channel.

10. The method of claim 6, wherein the nociceptive dorsal root ganglion neuron responds to capsaicin by elevating intracellular calcium flux or generates action potentials when polarized.

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caccgctttg caaagatgga taaag                                          25

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aattgcattc attttatgtt tca                                            23

11. The method of claim 9, wherein the capsaicin receptor is TRPV1.

12. The method of claim 1, further comprises contacting the immortalized cell with an agent that causes differentiation.

13. The method of claim 12, wherein the agent is cyclic AMP or an analog thereof or an agent that increases intracellular cAMP levels.

14. The method of claim 13, wherein the agent is forskolin.

15. A method of producing immortalized neuronal cells comprising:
   subjecting a neuronal cell to at least two rounds of electroporation to introduce a DNA segment wherein each round is followed by a step of recovery for a number of hours or days;
   selecting for neuronal cells that contain the DNA segment;
   introducing human telomerase reverse transcriptase into the selected cells;
   culturing the selected cell; and
   selecting for cells that contain human telomerase reverse transcriptase;
   thereby producing immortalized neuronal cells.

16. The method of claim 15, wherein the DNA segment is contained in a plasmid.

17. The method of claim 15, wherein the neuronal cells are selected from a group consisting of neuronal cells from the brain, neuronal cells from the spinal cord, dorsal root sensory ganglia, and autonomic ganglia.

18. The method of claim 13, wherein the DNA segment is an oncogene that is selected from the group consisting of Ras, Myc, Raf, and large T-Antigen.

19. A method of producing immortalized dorsal root ganglion neuronal cell line comprising:
   introducing by at least two rounds of electroporation, wherein each round is followed by a step of recovery for a number of hours or days, a plasmid comprising an SV40 large T-antigen into dorsal root ganglion cell;
   selecting dorsal root ganglion cells that contain the plasmid;
   introducing human telomerase reverse transcriptase into the selected cells;
   culturing the selected cell; and
   selecting for cells that contain human telomerase reverse transcriptase;
   thereby producing immortalized dorsal root ganglion neuronal line.

20. The method of claim 19, wherein human telomerase reverse transcriptase is introduced by a retrovirus.

* * * * *